United States Patent
Hurst et al.

(10) Patent No.: US 8,101,159 B2
(45) Date of Patent: *Jan. 24, 2012

(54) IN VIVO METHODS OF IDENTIFYING COMPOUNDS WHICH TARGET SUPPRESSED CANCER CELLS

(75) Inventors: Robert E. Hurst, Oklahoma City, OK (US); Michael A. Ihnat, Tuttle, OK (US)

(73) Assignee: The Board of Regents of the University of Oklahoma, Oklahoma City, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/540,821

(22) Filed: Aug. 13, 2009

(65) Prior Publication Data

US 2009/0311188 A1    Dec. 17, 2009

Related U.S. Application Data

(63) Continuation-in-part of application No. 11/642,313, filed on Dec. 19, 2006, now Pat. No. 7,575,926.

(60) Provisional application No. 60/751,698, filed on Dec. 19, 2005, provisional application No. 61/182,196, filed on May 29, 2009.

(51) Int. Cl.
| | |
|---|---|
| *A61K 49/00* | (2006.01) |
| *A61K 49/14* | (2006.01) |
| *A61K 31/33* | (2006.01) |
| *A61K 31/215* | (2006.01) |
| *A61K 31/165* | (2006.01) |
| *A61K 31/135* | (2006.01) |

(52) U.S. Cl. ......... 424/9.2; 514/183; 514/529; 514/617; 514/646

(58) Field of Classification Search .......... None
See application file for complete search history.

(56) References Cited

U.S. PATENT DOCUMENTS

| 6,156,744 | A  * | 12/2000 | Ross et al. ............ 514/183 |
| 6,232,523 | B1 * | 5/2001 | Tan et al. ............ 800/10 |
| 2006/0074041 | A1 | 4/2006 | Johnston et al. |
| 2008/0260853 | A1 | 10/2008 | Firestone |

FOREIGN PATENT DOCUMENTS

| WO | WO 00/06088 | 2/2000 |
| WO | WO 02/40717 | 5/2002 |
| WO | WO 2005/107743 | 11/2005 |

OTHER PUBLICATIONS

Loadman et al (Biochemical Pharmacology, 2000, vol. 59, pp. 831-837).*
Digby et al (Cancer Chemother Pharmacol, May 2005, vol. 56, pp. 307-316).*
Danson et al, Cancer Chemother Pharmacol, 2007, vol. 60, pp. 851-861).*
Clarkson et al., "Kinetics of proliferation of cancer cells in neoplastic effusions in man", *Cancer*, vol. 18, No. 10, pp. 1189-1213 (1965) abstract only.
Dansen, S., et al., "Validation of the comet-X assay as a pharmacodynamic assay for measuring DNA cross-linking produced by the novel anticancer agent RH1 during a phase I clinical trial", *Cancer Chemother Pharmacol* vol. 60, pp. 851-861 (Mar. 2, 2007).
Hurst, R., et al., "Matrix-dependent Plasticity of the Malignant Phenotype of Bladder Cancer Cells", *Anticancer Research*, vol. 23, pp. 3119-3128 (2003).
Hurst, R., et al., "A novel multidrug resistance phenotype of bladder tumor cells grown on Matrigel or SIS gel", *Science Direct Cancer Letters*, vol. 217, pp. 171-180 (2005).
Kyker, K., et al., "A model for 3-dimensional growth of bladder cancers to investigate cell-matrix interactions", *Urologic Oncology: Seminars and Original Investigations*, vol. 21, pp. 255-261 (2003).
Miller et al., "Use of tumor lines with selectable markers in assessing the effect on experimental metastases of combination chemotherapy with alkylating agents", *Clinical and Experimental Metastasis*, vol. 16, No. 5, pp. 480-488 (Jul. 1998) abstract only.

* cited by examiner

*Primary Examiner* — Karen Canella
(74) *Attorney, Agent, or Firm* — Dunlap Codding, P.C.

(57) ABSTRACT

In vitro and in vivo methods for identifying compounds capable of targeting suppressed cancer cells such as micrometastatic cells. The in vitro method includes the steps of comparing the response to a test compound of cancer cells grown on a suppressing cell support matrix which causes suppression of a malignant phenotype in a growing cancer cell and on a non-suppressing cell support matrix. The in vivo method includes a step of co-injecting labeled cancer cells with a malignant-phenotype suppressing matrix into a test animal to produce suppressed micrometastatic cells therein.

17 Claims, 11 Drawing Sheets

IN VIVO METHODS OF IDENTIFYING COMPOUNDS WHICH TARGET SUPPRESSED CANCER CELLS

CROSS-REFERENCE TO RELATED APPLICATIONS

This application is a continuation-in-part of U.S. Ser. No. 11/642,313, filed Dec. 19, 2006, now U.S. Pat. No. 7,575,926, which claims priority under 35 U.S.C. §119(e) to U.S. Provisional Application Ser. No. 60/751,698, filed on Dec. 19, 2005, each of which is hereby expressly incorporated by reference in its entirety.

The present application also claims priority under 35 U.S.C. §119(e) to U.S. Provisional Application Ser. No. 61/182,196, filed May 29, 2009, the entirety of which is hereby expressly incorporated herein by reference.

STATEMENT REGARDING FEDERALLY SPONSORED RESEARCH OR DEVELOPMENT

This invention was made with government support under Contract Nos. CA075822 and DK069808 awarded by the National Institutes of Health (NIH). The government has certain rights in the invention.

BACKGROUND

Most cancer deaths are caused by metastases, which are secondary tumors from cancer cells or clusters of such cancer cells that have broken off from the primary tumor and now are surviving at a distant site. Often these exist as micrometastases consisting of one or a few cells that are not growing or are growing very slowly or divide only at a rate sufficient for replacement thereof. Eventually, after some years or even decades, some of the micrometastases may begin to grow rapidly, forming tumors which eventually kill the patient. Micrometastases are notoriously resistant to traditional chemotherapeutic agents because the cells are not actively growing or expressing the malignant phenotype.

Currently, the drug development system for developing anticancer drugs is based on finding compounds that kill growing tumors. The initial step in developing an anticancer drug involves the screening of compounds against cancer cells growing in ordinary tissue culture on plastic. In vitro growth on plastic neglects the true physiological conditions under which tumors grow in the body, i.e., in contact with extracellular matrix. The extracellular matrix (ECM) in living tissues is the supporting material on which all cells grow and which interacts with cells to regulate their growth and how they assume their mature functions. Cancer cells remodel the extracellular matrix to be more conducive to growth of the cancer cells, and this process seems to represent a major requirement for them to be able to form a tumor.

For example, about 60,000 new cases of bladder cancer occur each year in the U.S. with about 13,000 deaths, placing it 5th overall in cancer incidence. In the United States, 98% of bladder cancers arise from the transitional epithelium of the bladder (transitional cell carcinoma, i.e., TCC). The general perception that bladder cancer is not serious is false. Some 15-25% of cases are invasive at diagnosis with one-fourth already having metastasized and with up to half developing metastatic tumors within two to three years. The 5-year survival of patients with metastatic bladder cancer is very low, about 20% with about a six-month median survival for even the most aggressive therapies. Of the 80-85% that are papillary, recurrence is high, up to 70% within 5 years in some studies, and of these, some 15%-25% will progress to invasive bladder cancer. Therapy achieves few cures, whether with BCG chemotherapy or neoadjuvant chemotherapy. The reasons for the high recurrence rate of bladder cancer are not known entirely, however, three mechanisms are suggested including underdiagnoisis by cystoscopy, a widespread "field defect" with continued promotion of new tumors or suppression of malignant cells, preventing their growth for a time.

To this end, the present invention is directed to novel in vitro and in vivo methods for identifying compounds capable of targeting living, phenotypically suppressed cancer cells, in particular, micrometastatic cells.

DETAILED DESCRIPTION OF THE INVENTION

Figure 1:
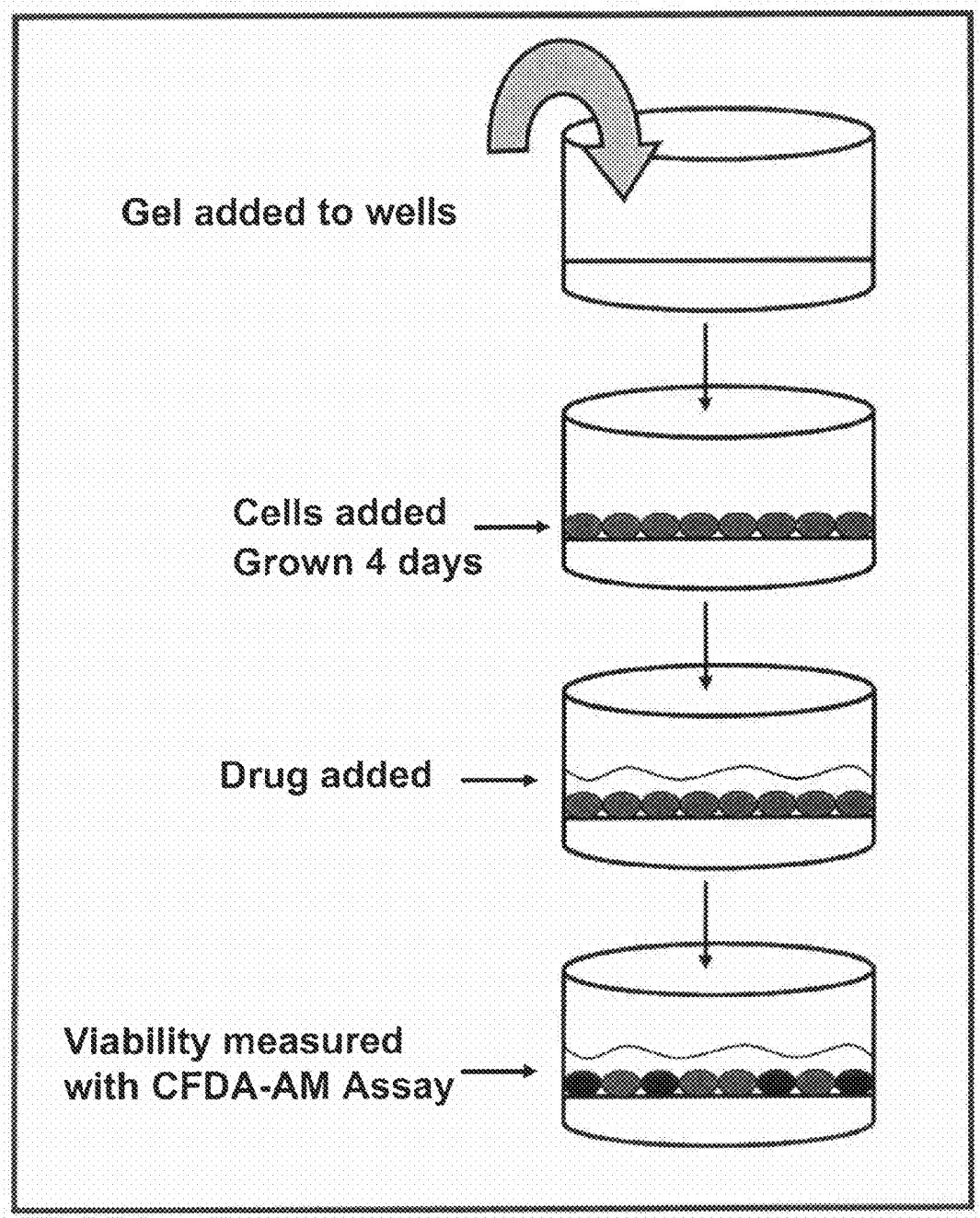
FIG. 1 is a pictorial representation of a test compound screening method of the present invention.

The present invention contemplates novel in vitro and in vivo methods for identifying compounds capable of targeting and attacking suppressed cancer cells. As used herein, the term "suppressed" refers to living cells or cell clusters which are not expressing their malignant phenotype. Examples of suppressed cancer cells include micrometastatic cells. Previous studies have shown that when cancer cells are grown on an extracellular matrix (ECM) preparation derived from normal (non-malignant) tissue ("normal ECM"), the malignant phenotype of the cells is suppressed and they radically change their appearance and growth characteristics to appear more normal. Cancer cells growing on this normal matrix are representative of suppressed micrometastatic cancer cells (cancer cells having a suppressed malignant phenotype). Finding compounds that are more active against cancer cells cultured on a normal matrix than they are against cells growing on plastic (or other "permissive" media) will identify compounds active against phenotypically suppressed micrometastases.

According to the present invention, test compounds are screened for the ability to target suppressed cancer cells that are representative of micrometastases and of recurrent tumors. The present invention presents methods for identifying anticancer drugs that will cure micrometastatic disease which is the true killer of many cancer patients. Additionally, the present invention allows relatively rapid screening of compounds that have weak activity against established primary tumors, but which are also more effective against micrometastatic disease.

The present invention is applicable in cancer research and drug development and solves the problem of providing a model that is more relevant to the biology of micrometastatic cells than is the conventional approach. Moreover, the strategy employed in the present invention of screening compounds specifically targets identification of compounds that will be active against metastatic tumors and recurrent tumors.

A primary advantage of the present invention is that, by screening test compounds using a matrix that suppresses the malignant phenotype of cancer cells, the compounds identified will be more active against the suppressed phenotype. This testing regimen provides for optimization of the development of novel anticancer drugs that specifically target recurrent and micrometastatic disease.

The present invention contemplates the use of any normal ECM material which has malignant-phenotype suppressing activity.

Mammalian tissue sources for ECMs which can be used in the invention are in general any tissue having an extracellular matrix that can be isolated from a mammal and de-cellularized. Thus for example, most mammalian organs are tissue sources. The tissue sources can be for example any mammalian tissue, including but not limited to, the small intestine, large intestine, stomach, lung, liver, glands, kidney, pancreas, placenta, heart, bladder, and prostate, and any fetal tissue from any mammalian organ (e.g., umbilical cord).

Natural ECM materials which can be used in the present invention include, but are not limited to, those produced from mammalian small intestine submucosa (SIS), stomach submucosa (SS), urinary bladder submucosa (UBS), dermis, or liver basement membranes (LBM) derived from sheep, bovine, porcine or any suitable mammal. Small intestine submucosa (SIS) is described for example in U.S. Pat. Nos. 4,902,508, 4,956,178 and 5,275,826. Urinary bladder submucosa (UBS) is described for example in U.S. Pat. No. 5,554,389. Stomach submucosa (SS) is described for example in U.S. Pat. No. 6,099,567. Liver submucosa (LS) or liver basement membrane (LBM) is described for example in U.S. Pat. No. 6,379,710. In the preparation process, native extracellular matrices are prepared so that their bioactivity is preserved, including many cellular and transcriptional and translational event. Assays for determining these activities are standard in the art.

Extracellular matrix can be obtained from the tissues of mammals by processes such as described for example in U.S. Pat. No. 5,554,389, U.S. Pat. No. 4,902,508, and U.S. Pat. No. 5,281,422. For example, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS).

Many of these ECM compositions are generally comprised of the same tissue layers and are prepared by the same method, the difference being that of the starting material. The matrices are generally decellularized in order to render them non-immunogenic, a process that preferably also retains some function of key proteins, such as some growth factors.

Other examples of ECM material suitable for use with the present invention include but are not limited to dermal extracellular matrix material, subcutaneous extracellular matrix material, large intestine extracellular matrix material, placental extracellular matrix material, ornamentum extracellular matrix material, heart extracellular matrix material, and lung extracellular matrix material, may be used, derived and preserved similarly as described herein for the SIS, SS, LBM, and UBM materials. Other organ tissue sources of basement membrane for use in accordance with this invention include spleen, lymph nodes, salivary glands, prostate, pancreas and other secreting glands. In general, as noted, any tissue of a mammal that has an extracellular matrix can be used for developing an extracellular matrix component of the invention.

Extracellular matrix material used in the present invention can comprise extracellular matrix combinations from such sources as, for example but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue (e.g., umbilical cord).

Preferably the ECMs of the inventions are fluidized or emulsified and have a gel consistency similar to the preparation of fluidized intestinal submucosa, as described in U.S. Pat. No. 5,275,826. The UBS is comminuted by tearing, cutting, grinding, shearing or the like. Grinding the UBS in a frozen or freeze-dried state is preferred although good results can be obtained as well by subjecting a suspension of submucosa pieces to treatment in a high speed (high shear) blender and dewatering, if necessary, by centrifuging and decanting excess water. Additionally, the comminuted fluidized tissue can be solubilized by enzymatic digestion of the bladder submucosa with a protease, such as trypsin or pepsin, or other appropriate enzymes for a period of time sufficient to solubilize said tissue and form a substantially homogeneous solution.

Although these particular ECMs are known and have been isolated and used, there may be other mammalian tissues from which extracellular matrix can be isolated and prepared and as such would be suitable for the purposes of the present invention.

The present invention is further directed to methods of treating subjects in need of treatment for micrometastatic (suppressed) cancer cells by treatment with particular compounds, for example as identified by the methods of the present invention.

In Vitro Screening Method

Figure 4:
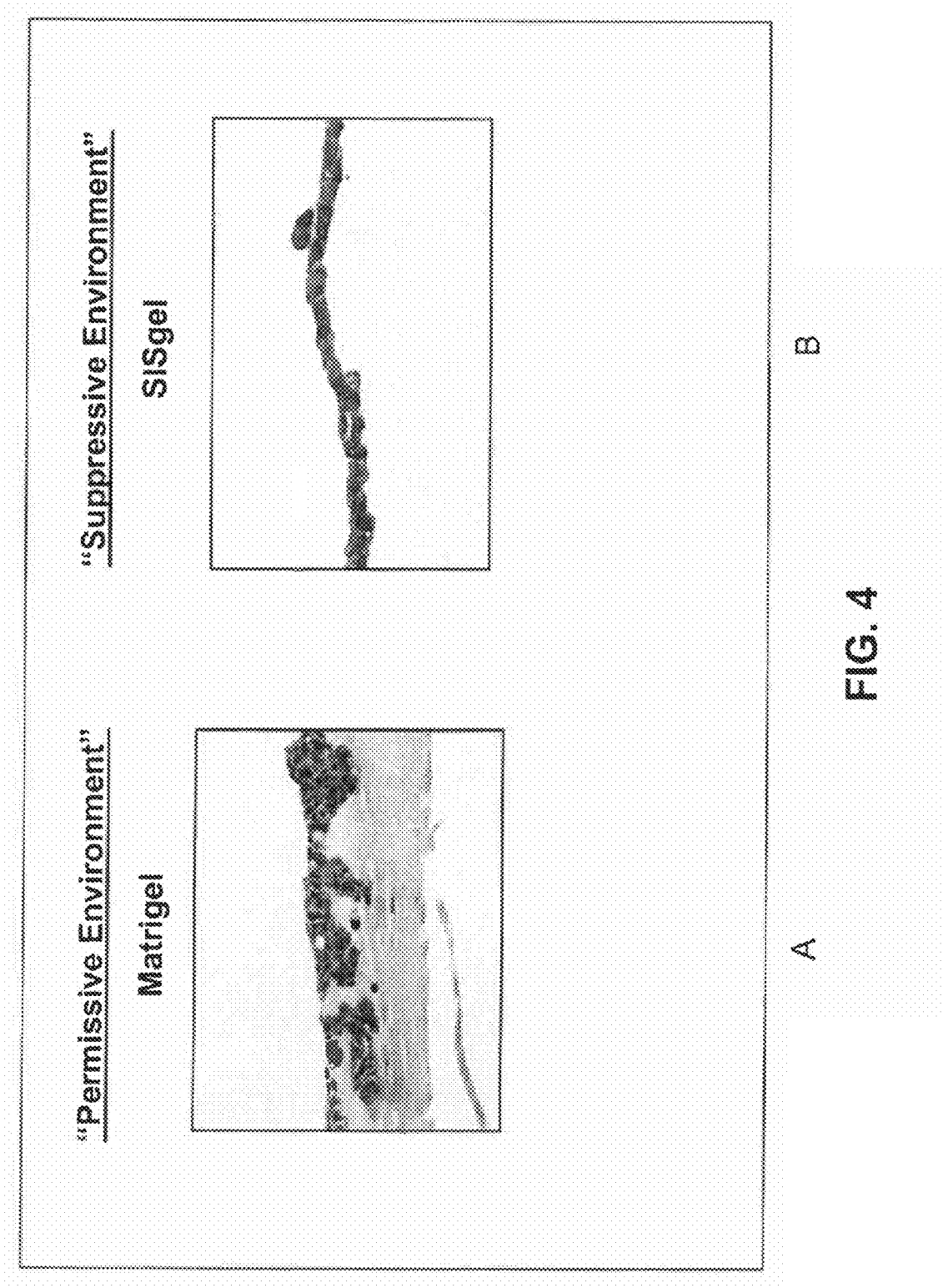
FIG. 4A is a micrograph showing cell growth on a non-suppressing cell support matrix.
FIG. 4B is a micrograph showing cell growth on a suppressing cell support matrix.
Figure 7:
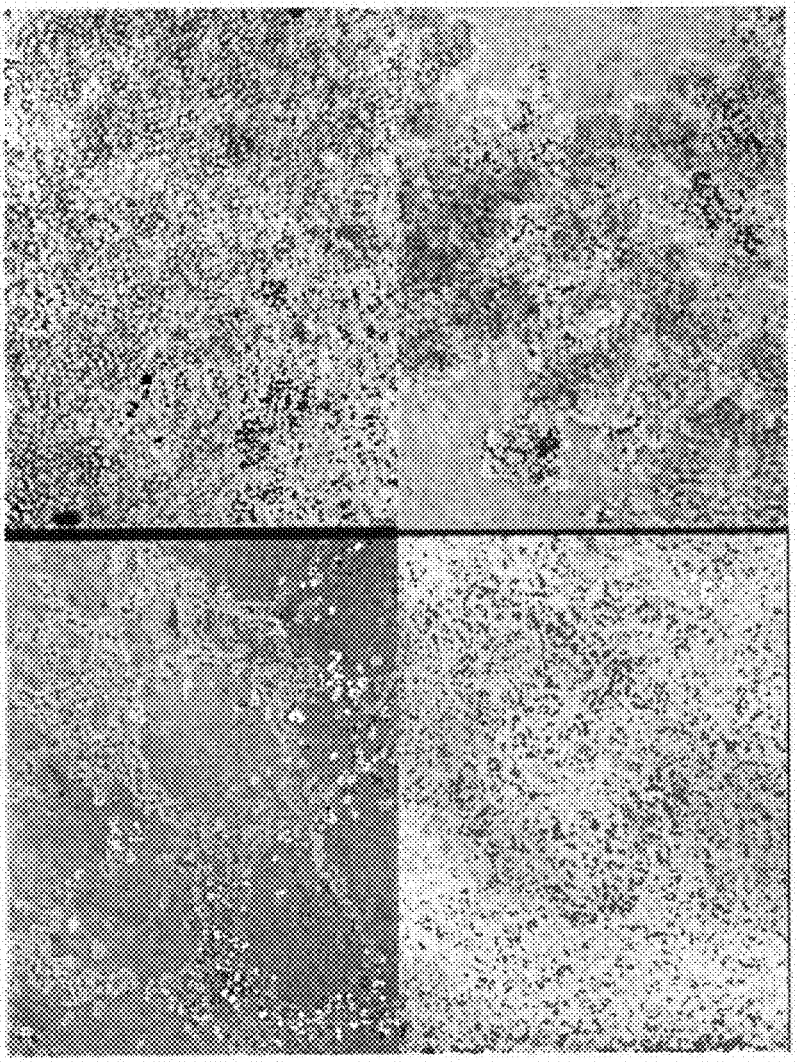
FIG. 7 is a micrograph showing morphology changes of MDA-breast cancer cells and B16-F10 melanoma cells on Matrigel and SISgel.

An in vitro method of the invention comprises a method for identifying a compound which preferentially targets cancer cells having a suppressed malignant phenotype is shown, schematically in FIG. 1. The in vitro method includes the steps of, in a first culture system, providing a suppressing cell support matrix (a "normal" ECM) which causes suppression of a malignant phenotype in a growing cancer cell. Commercially available examples of suppressing cell support matrices include, but are not limited to, SISgel (produced from small intestine submucosa and commercially available from Cook Biotech), Humatrix, Amgel, and similar support media (FIGS. 4B and 7). Other ECMs which may be used in the invention are discussed above. Shown in FIG. 4B is growth of J82 cells from a highly aggressive tumor wherein growth on SISgel suppresses the malignant phenotype and models conditions found by metastasizing cells which must overcome suppressive effects of local extracellular matrix. Shown in FIG. 7 is growth of MDA-MB-468 breast cancer cells and B16-F10 skin tumor cells (metastatic murine melanoma) wherein growth on SISgel suppresses the malignant phenotype and models conditions found by metastasizing cells which must also overcome suppressive effects of local extracellular matrix (i.e., Matrigel). Examples of other cell lines exhibiting similar behavior as that of J82, MDA-MB-468, and B16-F10 cell lines and in which the test compounds have been shown to be active against include RT4 cells, TCCSUP cells, and 5637 cells.

The in vitro method further includes the step of providing a cell-nutrient mixture having a quantity of cancer cells disposed in a nutrient media. Examples of cancer cells which may be used include, but are not limited to, bladder cancer cells, liver cancer cells, breast cancer cells, lung cancer cells, prostate cancer cells, pancreatic cancer cells, colon cancer cells, melanoma, or other transitional cancer cells, squamous cancer cells, small cell carcinoma cells, medullary cancer cells, adenocarcinomas, basal cell carcinomas or any other metastatic cell line, micrometastatic cell lines, or other cell lines derived from a secondary tumor. A first portion of the cell-nutrient mixture is combined with (layered on top of) the suppressing cell support matrix thereby forming a suppressing matrix-cell mixture (bilayered system). The suppressing matrix-cell mixture (bilayered system) is incubated for a period of time to allow growth of the cells while causing suppression of the malignant phenotype in the cancer cells thereby forming a suppressed cancer cell culture. A test compound is added to the suppressed cancer cell culture forming a treated suppressed culture. The treated suppressed culture is incubated for a period of time forming an incubated treated suppressed culture.

The in vitro method of the present invention further includes the step of, in a second culture system, providing a non-suppressing cell support matrix which allows expression of a malignant phenotype in a growing cancer cell. Examples of non-suppressing cell support matrices include, but are not limited to, plastic (as known to those of ordinary skill in the art), Matrigel and similar support media (FIGS. 4A and 7). Shown in FIGS. 4A and 7, respectively, is growth of J82, MDA-MB-468, and B16-F10 cells from highly aggressive tumors on Matrigel recapitulating in vivo phenotype of the original tumor. A second portion of the cell-nutrient mixture is combined with (layered on top of) the non-suppressing cell support matrix forming a non-suppressing matrix-cell mixture (bilayered system). The non-suppressing matrix-cell mixture (bilayered system) is incubated for a period of time to allow growth of the cells and expression of the malignant phenotype in the cancer cells thereby forming a non-suppressed cancer cell culture. The test compound is added to the non-suppressed cancer cell culture forming a treated non-suppressed culture. The treated non-suppressed culture is incubated for a period of time thereby forming an incubated treated non-suppressed culture. The number (or survival) of suppressed cancer cells in the incubated treated suppressed culture is compared with the number (or survival) of non-suppressed cancer cells in the incubated treated non-suppressed culture.

Preferably, the method further includes the step of concluding that the test compound is positive (i.e., preferentially targets suppressed cancer cells) when the number or survival of cancer cells in the incubated treated non-suppressed culture exceeds the number or survival of cancer cells in the incubated treated suppressed culture or, conversely, when cell mortality of the suppressed culture exceeds the cell mortality in the non-suppressed culture. For example, a threshold for concluding that suppressed cancer cells are preferentially targeted is when the number (or survival) of cancer cells in the incubated treated non-suppressed culture is at least twice the number (or survival) of cancer cells in the incubated treated suppressed culture. A positive test compound is preferably confirmed via a full-dose response curve performed in a different, non-suppressing cell-support matrix preparation such as, for example, Matrigel, plastic, or other material or media for screening increased activity of the test compound when compared to the test compound's activity in the suppressing cell support matrix, or the test compound may be further assessed using the in vivo method described below.

The in vitro method includes the step of providing a non-suppressed cancer cell culture comprising actively growing cancer cells which have the malignant phenotype, wherein the malignant phenotype of the cancer cells is expressed. In the in vitro method, the suppressed cancer cell culture and the non-suppressed cancer cell culture are each treated with a test compound (as set forth hereinabove) and incubated. The number or survival of cancer cells in the treated suppressed cancer cell culture is compared with the number or survival of cancer cells in the treated non-suppressed cancer cell culture or, conversely, when cell mortality of the suppressed culture exceeds the cell mortality in the non-suppressed culture.

In addition, the in vitro embodiment of present invention includes the step of concluding that the test compound preferentially targets cancer cells having suppressed malignant phenotypes when the number or survival of cancer cells in the treated non-suppressed cancer cell culture exceeds the number or survival of cancer cells in the treated suppressed cancer cell culture.

In Vivo Screening Method

In traditional screening methods, potential cancer drugs are tested on flank xenografts that are grown by co-injecting cancer cells with Matrigel under the skin of immunocompromised mice on the flank. The Matrigel is an ECM product derived from a sarcoma that provides a "cancer-friendly" environment. Without Matrigel, most cancer cell lines will die if injected under the skin in this manner. With the Matrigel, tumors will form that can be used to test efficacy of conventional drugs. However, this traditional approach will not be successful in identifying drugs that specifically target the ECM-suppressed cancer cell (which mimics the micrometastatic condition).

The in vivo screening method of the present invention comprises co-injecting both cancer cells with a suppressing ECM material under the flank skin of immunocompromised mice. This is a non-obvious, inventive, step because it is known that cancer cells co-injected with saline or with nutrient solutions into an immunocompromised mouse model will generally die within a few days.

Normally, cancer cells that do not grow will die. However, it is a particular discovery of the present invention that when cancer cells are co-injected with a suppressing ECM material such as described above, they will remain alive under the flank skin for weeks but will not grow in a malignant fashion. The cells used in the present method are preferably transfected with a gene for a fluorescent protein such as Green Fluorescent Protein (GFP) to facilitate imaging the cells in vivo. However, other labels including, but not limited to, Red Fluorescent Protein (RFP), luciferase, and IR-emitting proteins such as katushka, may also be used. Alternatively, the cancer cells may be labeled non-genetically using external labeling mechanisms such as antibodies which are specific for particular cancer cells. The animals are then treated with a test compound identified for screening, preferably one which has been identified previously as preferentially targeting ECM-suppressed cancer cells, for example by using the present in vitro method described elsewhere herein. The effectiveness of the test compound in preferentially killing the suppressed cancer cells versus the control is then assessed. The test compound can also be tested in a Matrigel co-injection xenograft model to determine whether or not it is also active against actively growing cancer cells. If this is the case, such activity represents a bonus.

Any immunocompromised animal such as, but not limited to, mice and rats may be used herein. There are other possible animal models than the immunocompromised mouse or rat. Immunocompromised animals lack a functioning immune system and therefore will not reject human cancer cells implanted in them. One strain of these animals lack hair and therefore are referred to a "nude mice". Other strains are severely compromised immunodeficient (SCID) mice. An immunodeficient rat also exists that can be used. The problem of rejecting tumors can be avoided by transplanting a mouse tumor derived from a genetically identical strain of mice. Because the animals are all identical, a tumor will not be rejected provided it was derived form the same strain of animals. A third possibility is to genetically engineer mice to have a high susceptibility to cancer. Such animals provide an alternative natural model for development of metastasis versus the transplanted models.

Where used herein, the term "survival" refers to the percentage of cells or animals which are alive after a course of treatment. Conversely, "mortality" refers to the percentage of cells or animals which have died after a course of treatment.

The present invention further contemplates a kit comprising the suppressing cell support matrix, the non-suppressing cell support matrix, and the cell-nutrient mixture, wherein the cell-nutrient mixture and the suppressing and non-suppressing cell support matrices can be combined and incubated as described above.

In another embodiment, the present invention contemplates a kit wherein portions of the cell-nutrient mixture are pre-mixed with the cell-support matrices to form a suppressing matrix-cell mixture and a non-suppressing matrix-cell mixture which are refrigerated (or otherwise handled) for a period of time to prevent active cell growth. The mixtures may be plated for providing ready-to-use test cultures to which test compounds may be applied. As noted, each mixture, or each suppressing test culture and non-suppressing test culture may be refrigerated for suspension of cell growth until used in the methods described herein.

Figure 6:
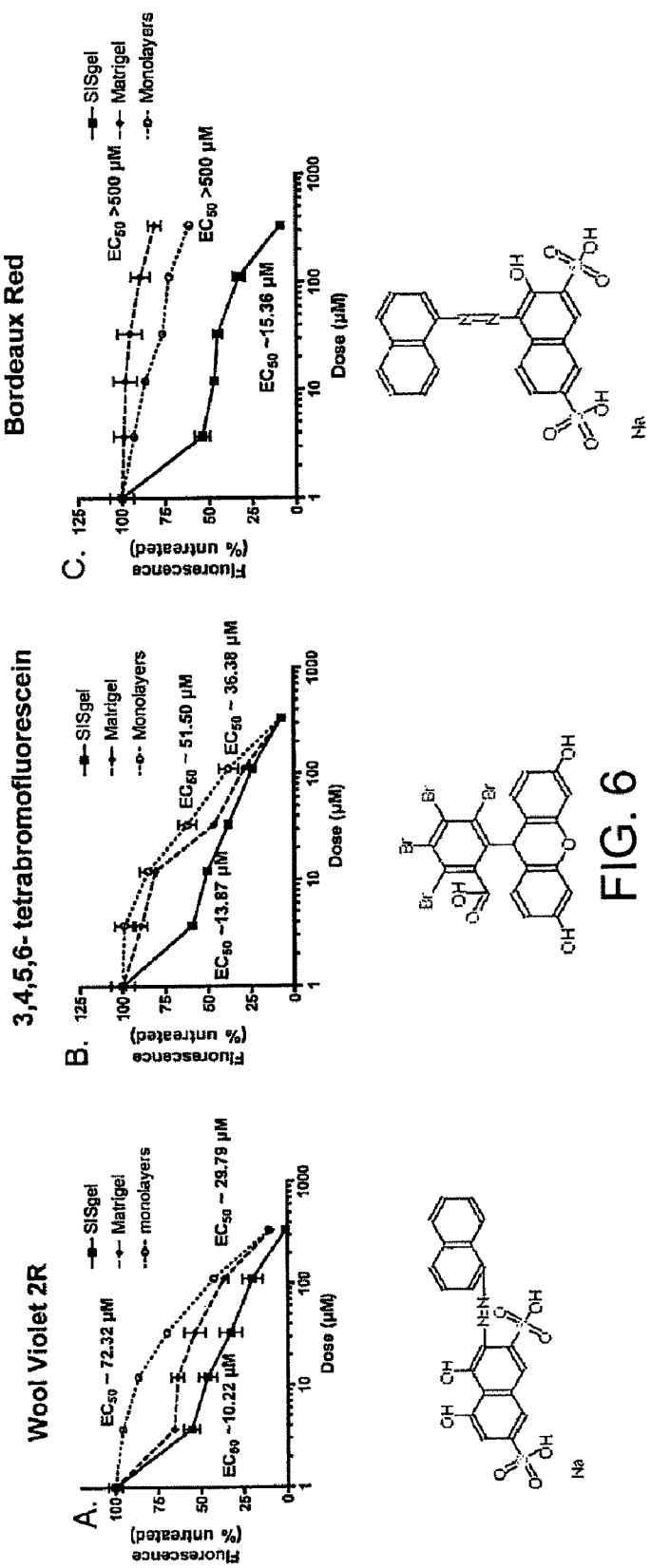
FIGS. 6A-6C are Full Dose-Response Curves identifying three lead compounds for attacking suppressed cancer cells.

The present invention further contemplates a method of treating bladder cancer, liver cancer, breast cancer, lung cancer, prostate cancer, pancreatic cancer, colon cancer, melanoma, or any cancer including, but not limited to, those involving transitional cells, squamous cells, small cell carcinoma cells, medullar cells, adenocarcinomas, and basal cell carcinomas, wherein the method includes administering to a subject in need of such treatment a composition comprising one or more of the compounds selected from the group consisting of NSC191384, NSC19134D-1, NSC19134D-2, NSC19134D-3, NSC 606532, NSC 697726, and NSC 140377 (see FIGS. 3A and 3B), Wool Violet 2R, 3,4,5,6-tetrabromofluorescein, and Bordeaux Red, (see FIGS. 6A-6C). The composition preferably further comprises a pharmaceutically acceptable carrier within which the compound is disposed.

While the invention is described herein in connection with certain embodiments and examples so that aspects thereof may be more fully understood and appreciated, it is not intended that the invention be limited to these particular embodiments and examples. On the contrary, it is intended that all alternatives, modifications and equivalents are included within the scope of the invention as defined herein. Thus the examples described herein, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention. Changes may be made in the formulation of the various compositions described herein or in the steps or the sequence of steps of the methods described herein without departing from the spirit and scope of the invention as described herein.

Experimental

In Vitro Screening Method

Cell culture. All tissue culture media and supplements were from Invitrogen, Rockville, Md. Matrigel was obtained from Becton-Dickinson (Bedford, Mass.). SISgel was obtained from Cook Biotech (W. Lafayette, Ind.). TCC-SUP, J82, and 5637 cells were obtained from the American Type Culture Collection (ATCC).

Flank xenograft model. J82 cells stably expressing green fluorescent protein (GFP) were prepared as follows. pLE-GFP-C1 retrovirus (Clontech, Mountain View, Calif.) was co-transfected with the pVSV-G vector (Clontech, Mountain View, Calif.) which contains a viral envelope gene into the packaging cell line GP2-293 (Clontech, Mountain View, Calif.). Supernatant from the packaging cells containing the infective virus was collected every 24 hours for 4 days. Fluorescent target cells were made by infecting J82s, a urothelial transitional cell carcinoma cell line (ATCC, Manassas, Va.), with 1 ml of fresh, virus containing, supernatant/well containing 100,000 target cells along with 8 µg/ml of polybrene (Sigma Aldrich, St. Louis, Mo.). Each application of viral supernatant was filtered through a 0.4 µM syringe filter before application to target cells. Supernatant was removed and fresh virus containing media replenished on target cells every 24 hours until 4 changes of media were completed. Virus containing media was replaced with Minimum Essential Media, MEM, (Life Technologies, Carlsbad, Calif.) containing 1% nonessential amino acids, 1% L-glutamine, 1% sodium pyruvate and 10% Fetal Calf Serum, and cells were allowed to grow to 90% confluence. Stable transfects were selected through sequential sorting and enrichment of fluorescent cells using flow cytometry.

In sterile 500 µl centrifuge tubes, placed on ice, 100 µl of cell suspension was mixed with either 100 µl ice-cold prepared SISgel or ice-cold Matrigel and mixed well. The mix was immediately injected into either the right or left flank of a 5-week old nude mouse, nu/nu-nuBR, (Charles River Laboratories, Wilmington, Mass.). Caliper measurements of tumor size were taken every week for the length of the study as were fluorescent images. Images were visualized with the Lightool's LT-9900 system (Lightools, Encinitas, Calif.) with the EGFP filter set of 470 nm excitation filter and 515 nm viewing filter and captured with a Nikon DC290 digital camera. The area and intensity of the tumor was measured using Adobe Photoshop by first selecting the tumor area, then counting pixels above a threshold selected to eliminate background, non-tumor areas. The integrated intensity was calculated by multiplying the average intensity of detected pixels by the number of pixels detected.

Plating of cells for screening. Three-dimensional gel cultures with Matrigel were made by layering 50 µl of ice cold Matrigel into wells of a Costar 3610 white, clear bottom 96-well plates (Corning, Corning, N.Y.) allowed to gel at 37° C. Confluent cells were trypsinized with 1 ml 0.25% trypsin −1 mM EDTA, and 30,000 were added to wells containing the gelled matrices. The cells were fed with 50 µl of their respective media containing 10% fetal calf serum. To establish non-confluent monolayers, cells were plated at a cell density of 10,000/well 24 hours prior to drug treatments.

Screening of compounds. The National Cancer Institute Developmental Therapeutics Program (NCI DTP) diversity set of 1990 compounds1 was obtained by material transfer agreement and was diluted to a final concentration of 166.7 µM in serum-containing media and placed onto cells for 72 hours at 37° C. and 5% CO2. A marker of cell proliferation using the substrate 5-carboxyfluorescein diacetate acetoxymethyl ester (CFDA-AM) cleaved to fluorescein by non-specific cellular esterases was used. Briefly, media containing a final concentration of 5 µM CFDA-AM (Molecular Probes, Eugene, Oreg.) was added in PBS for two h at 37° C. Plates were then read by a FLUOstar Optima plate reader (BMG LABTECH, Durham, N.C.) using 385 nm excitation, 428 nm emission filter.

Dose-response relations of lead compounds. To 100 µl media on cells was added 100 µl of a 2× (666.7 µM) stock of either doxorubicin, tetrandrine or o-cresolphthalein in completed media in a single column in a 96-well plate. 1:3 dilutions were made from this highest dose by removing 66.7 µl into the next column of cells containing 133 µl media. Cells were incubated with drug for 72 hours, then the CFDA-AM assay completed as described above.

Data Analysis and Statistics.

Drug screening. The percent inhibition of cell proliferation (as determined by CFDA-AM cleavage) as compared to untreated cells was calculated for each drug in the wells of plates. The ratio of percent inhibition of the same drug of cells grown on SISgel as compared to non-confluent monolayers also was calculated. All library compounds were screened twice for consistency.

Dose-response relations. Data were graphed as percent inhibition of proliferation as compared to untreated cells and from this EC50 values calculated using sigmoidal dose-response non-linear regression analysis (GraphPad Prism 4.0 software, San Diego, Calif.). Dose-response relation data were compared to one another using two-way ANOVA with Bonferroni post-test (GraphPad Prism 4.0 software, San Diego, Calif.).

EXAMPLES

SISgel (90 µl) is added to wells of a 96-well plate and allowed to gel. Cancer cells in 50 µl of nutrient (such as, for example, J82 bladder cancer cell, RT4 cancer cells, TCCSUP cancer cells, 5637 cancer cells, MDA-MB-468 breast cancer cells, or B16-F10 skin tumor (or any metastatic murine melanoma)) are added to each well and allowed to attach and grow. After 24 hours, the test compounds are added to wells at 10 µM concentration. The cells are allowed to grow in the presence of the test compound for 24 hours, at which time the number of cells (or survival or mortality) are estimated by a fluorometric method. In one embodiment, the fluorometric method is an assay performed using an esterase substrate, 5-carboxyfluorescein diacetate acetoxymethyl ester (CFDA) (available from Molecular Probes, Eugene, Oreg., USA), however, any suitable assay for measuring cell survival or mortality known by those of ordinary skill in the art may be used. Examples of fluorometers which can be used include, but are not limited to, FLUOStar Optima plate reader (BMG Biotech), FL600 fluorescent plate reader (Bio-Tek Instruments), Victor2 plate reader (Wallac), FluoroCount BF10000 fluorescent microplate reader (Packard), CytoFluor® 4000 (Applied Biosystems), Bio-Tek Synergy, BMG FLUOstar Galaxy and OPTIMA, PerkinElmer Victor™, PerkinElmer HTS 7000, TECAN SpectraFluor Plus, Thermo LabSystems Fluoroskan Ascent, and the like.

The cell number results are compared to those observed in cells grown conventionally on plastic in nearly confluent monolayers that show approximately the same growth rate as the cells on SISgel. In this embodiment, a greater than two-fold difference (SISgel:monolayer ratio, see FIG. 5, for example) in cell death (mortality) between cells grown on SISgel and on plastic (i.e., presence of at least twice as many living cells on the plastic culture) is interpreted as indicating that the compound is positive, i.e., it targets suppressed cells. In other embodiments, the ratio used may be, for example, less than two fold or greater than two fold as long as the cell number or survival on non-suppressing cell support matrix is greater than the number of cells on the suppressing cell support matrix. Preferably, each positive result is then confirmed by a full dose-response curve.

The dose-response curve of those test compounds that are confirmed as targeting cells growing on the suppressing cell support matrix are then determined in Matrigel, Vitrogen 100 (collagen gel), or any other non-suppressing cell support matrix, preferably wherein the cell support matrix is a cancer-derived matrix. Matrigel, for example, is a cancer-derived extracellular matrix preparation in which the cancer cells express the full malignant phenotype. Test compounds that show a greater effect on cells grown in SISgel than in Matrigel or on plastic (i.e., are positive) are then referred to as lead compounds. The lead test compounds can be administered shortly after metastatic tumors are established, identified, or purported to exist and are small and still likely in the suppressed state.

Results

Figure 2:
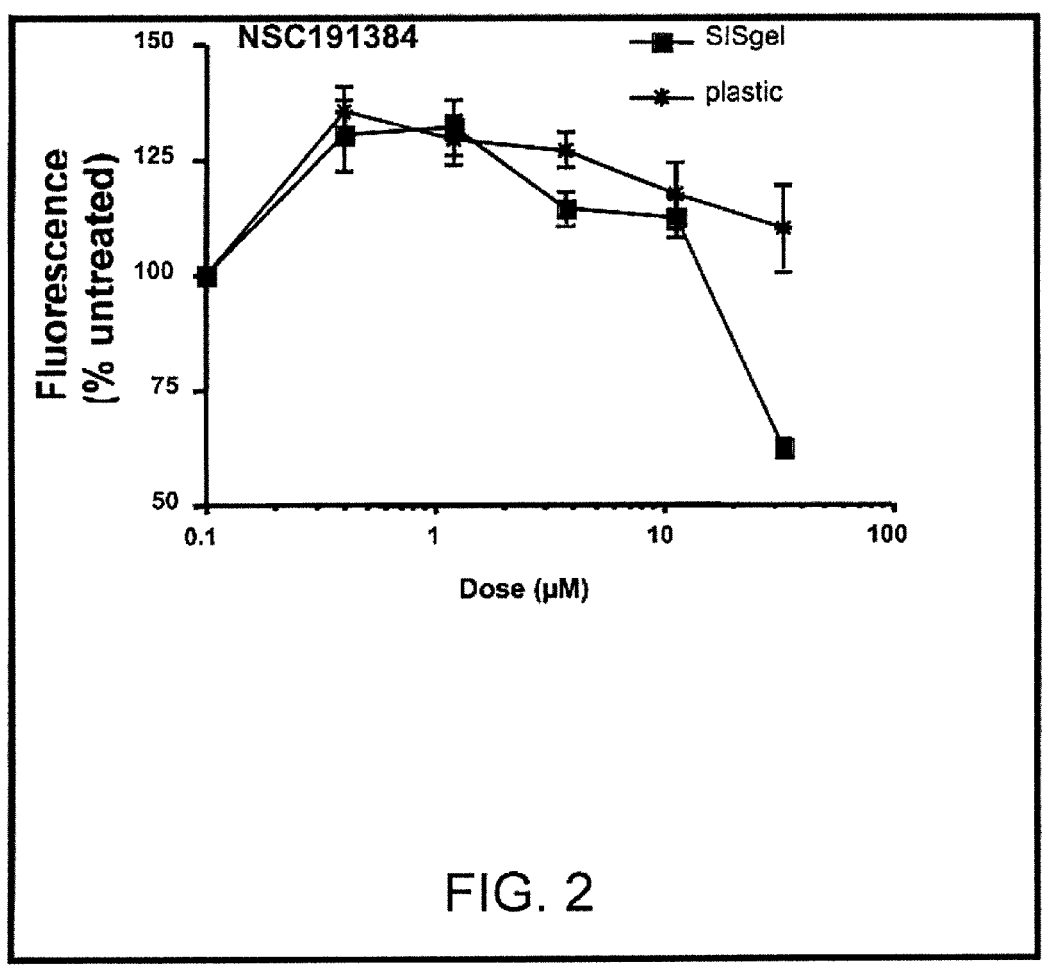
FIG. 2 is a graph of a Full Dose-Response Curve.

The present invention contemplates a high-throughput approach to screening compounds. FIG. 2 shows a representative cell proliferation dose-response curve of a lead compound (NSC191384) on J82 cells grown on SISgel and as non-confluent monolayers compiled after screening over 2000 compounds from two libraries of compounds with anti-cancer activity obtained from the National Institute of Health. The dose-response data confirms that the test compound is more active against cancer cells grown under the suppressing conditions than it is against cancer cells grown in conventional, non-suppressing cell culture (expressing malignant phenotypical characteristics) and drug screening.

Figure 3A:
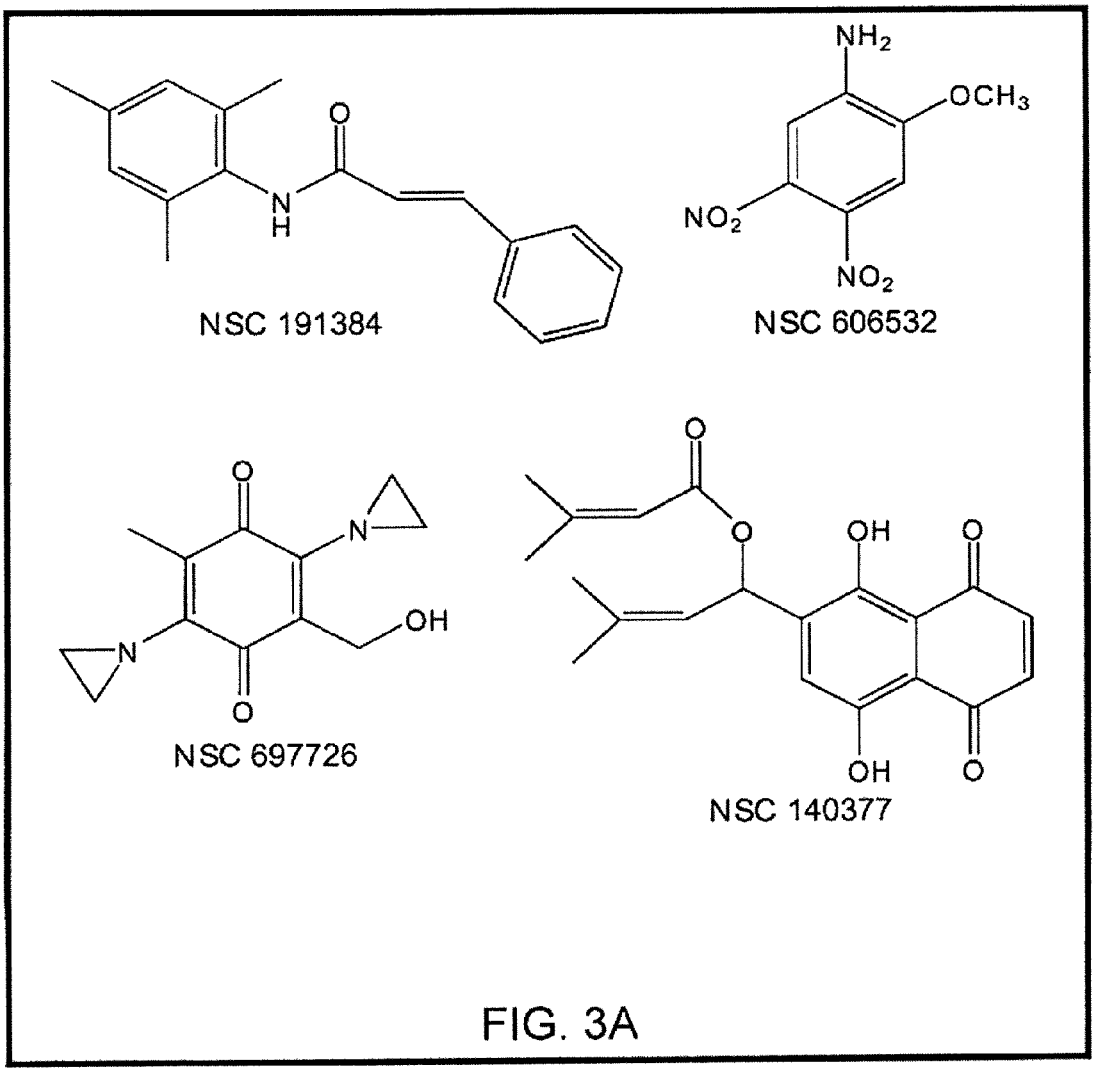
FIG. 3A shows chemical structures of four test compounds.
Figure 3B:
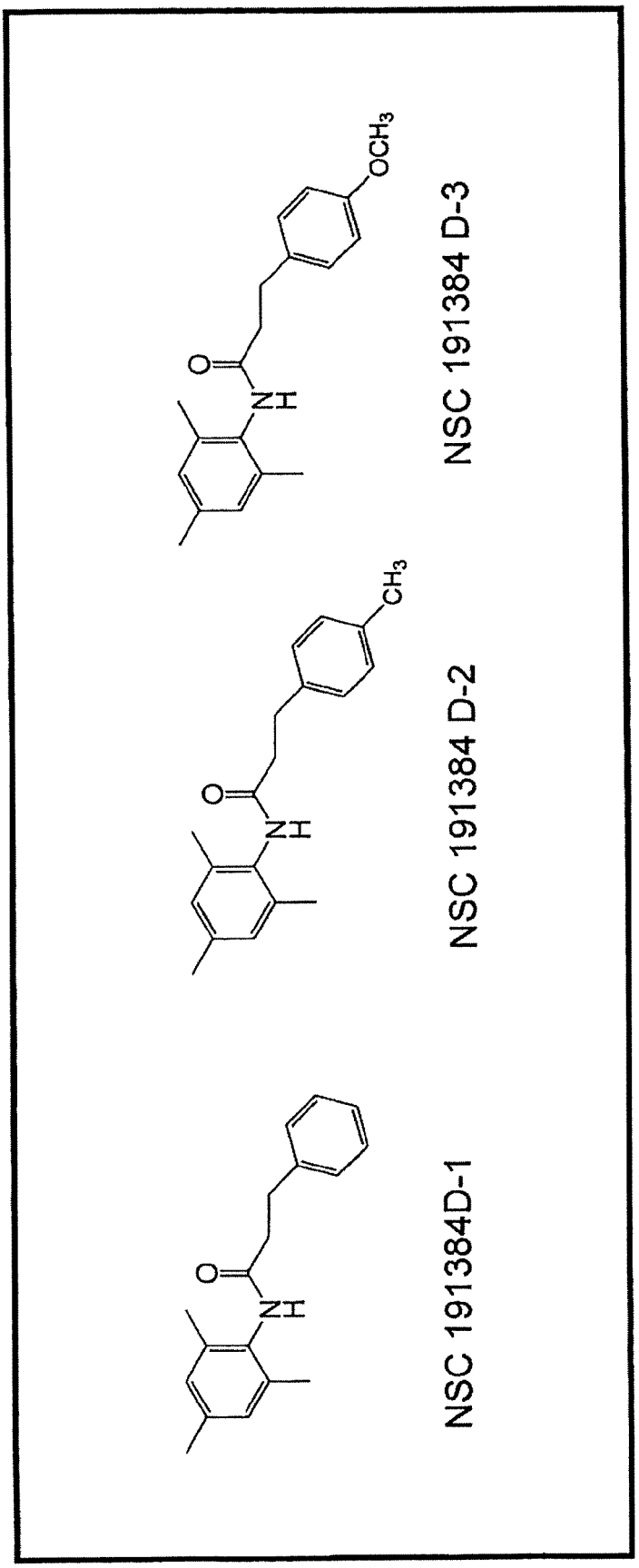
FIG. 3B shows chemical structures of three derivatives of Compound NSC191384 of FIG. 3A.

FIGS. 3A and 3B show seven lead compounds (NSC 191384, NSC 606532, NSC 697726, NSC140377, NSC191384D-1, NSC191384D-2, and NSC191384D-3) that have been identified having several fold increased sensitivity against cells on normal matrix than against cells grown on plastic.

Figure 5:
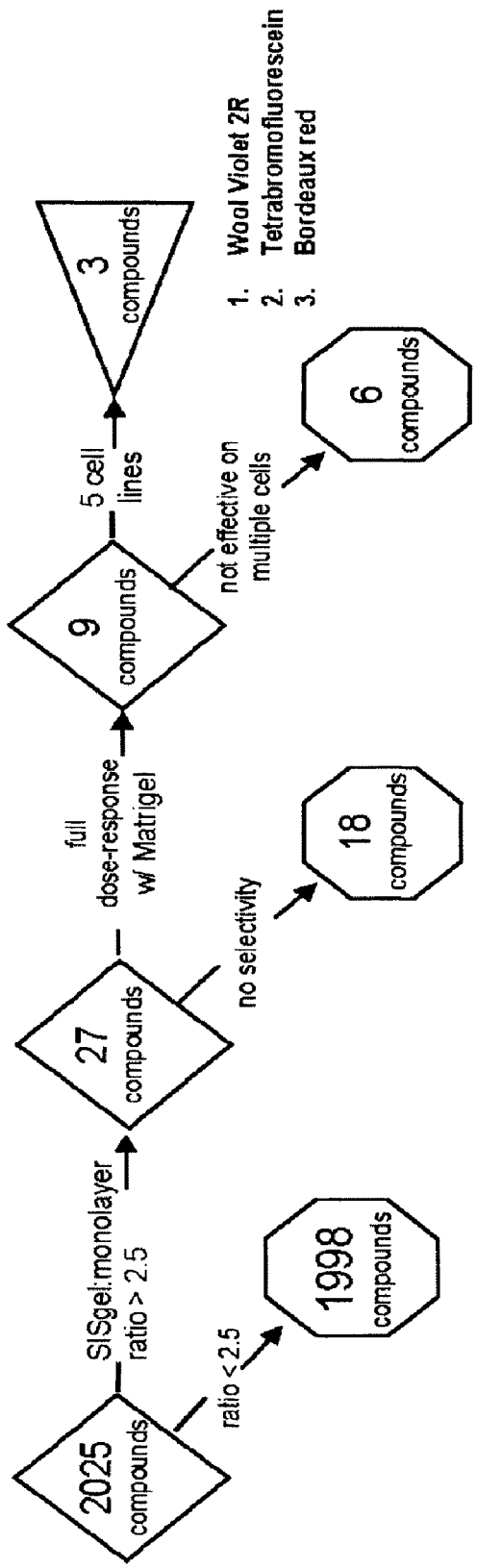
FIG. 5 is a flowchart showing results of a chemical library screen.

FIG. 5 is a flowchart showing results of a chemical library screen wherein additional lead compounds Wool Violet 2R, 3,4,5,6-tetrabromofluorescein, and Bordeaux Red have been identified.

FIGS. 6A-6C show representative cell proliferation dose-response curves of additional lead compounds Wool Violet 2R, 3,4,5,6-tetrabromofluorescein, and Bordeaux Red that have been identified having several fold increased sensitivity against cells on normal matrix than against cells grown on plastic.

FIG. 7 shows that the growth of cells in SISgel produced a significantly different phenotype than cells grown in Matrigel. Cells in SISgel grew as a monolayer and cells grown on Matrigel either forming a 3-dimensional lattice (MDA-MB-468) or grow in 3-dimensional sheets (B16-F10).

Figure 8:
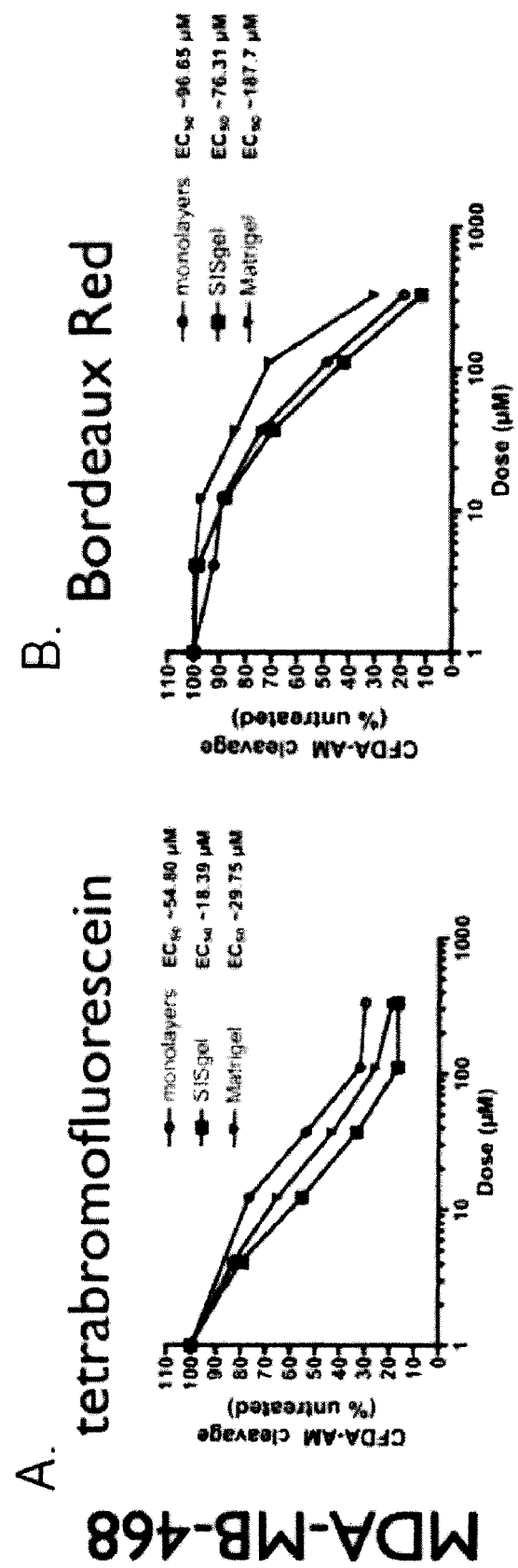
FIGS. 8A-8B are Full Dose-Response curves identifying two lead compounds for attacking suppressed MDA-MD-468 breast cancer cells.

FIGS. 8A and 8B show complete dose response relations of tetrabromofluorescein and Bordeaux Red indicating that MDA-MB-468 cells grown in SISgel were more sensitive to these compounds as indicated by lower EC50 values (defined as the molar concentration of agonist, which produces 50% of the maximum possible response dose for that agonist) as compared to cells grown as monolayers or in Matrigel.

Figure 9:
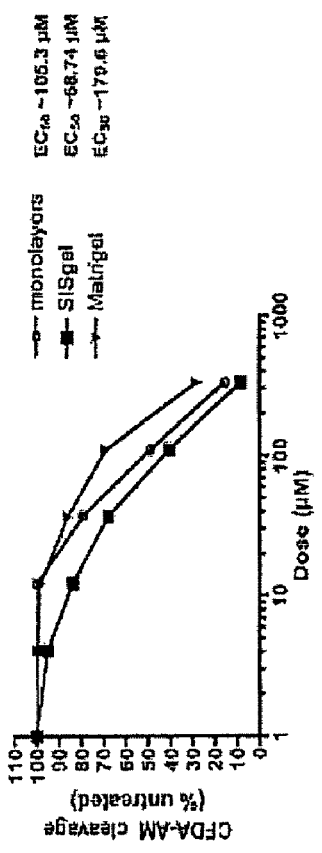
FIGS. 9A-9B are Full Dose-Response curves identifying two lead compounds for attacking suppressed B16-F10 melanoma cells.
Figure 9:
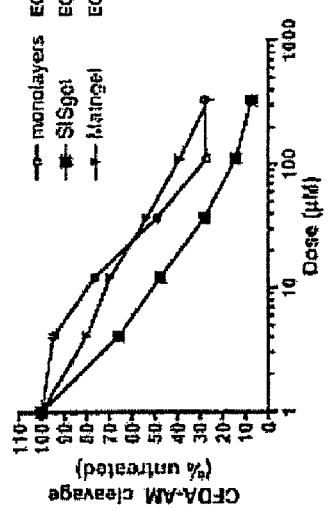

FIGS. 9A and 9B show complete dose response relations of tetrabromofluorescein and Bordeaux Red and indicating that B16-F10 cells grown in SISgel were more sensitive to the lead compounds as indicated by lower EC50 values as compared to cells grown as monolayers or in Matrigel.

In Vivo Screening Method

Figure 10:
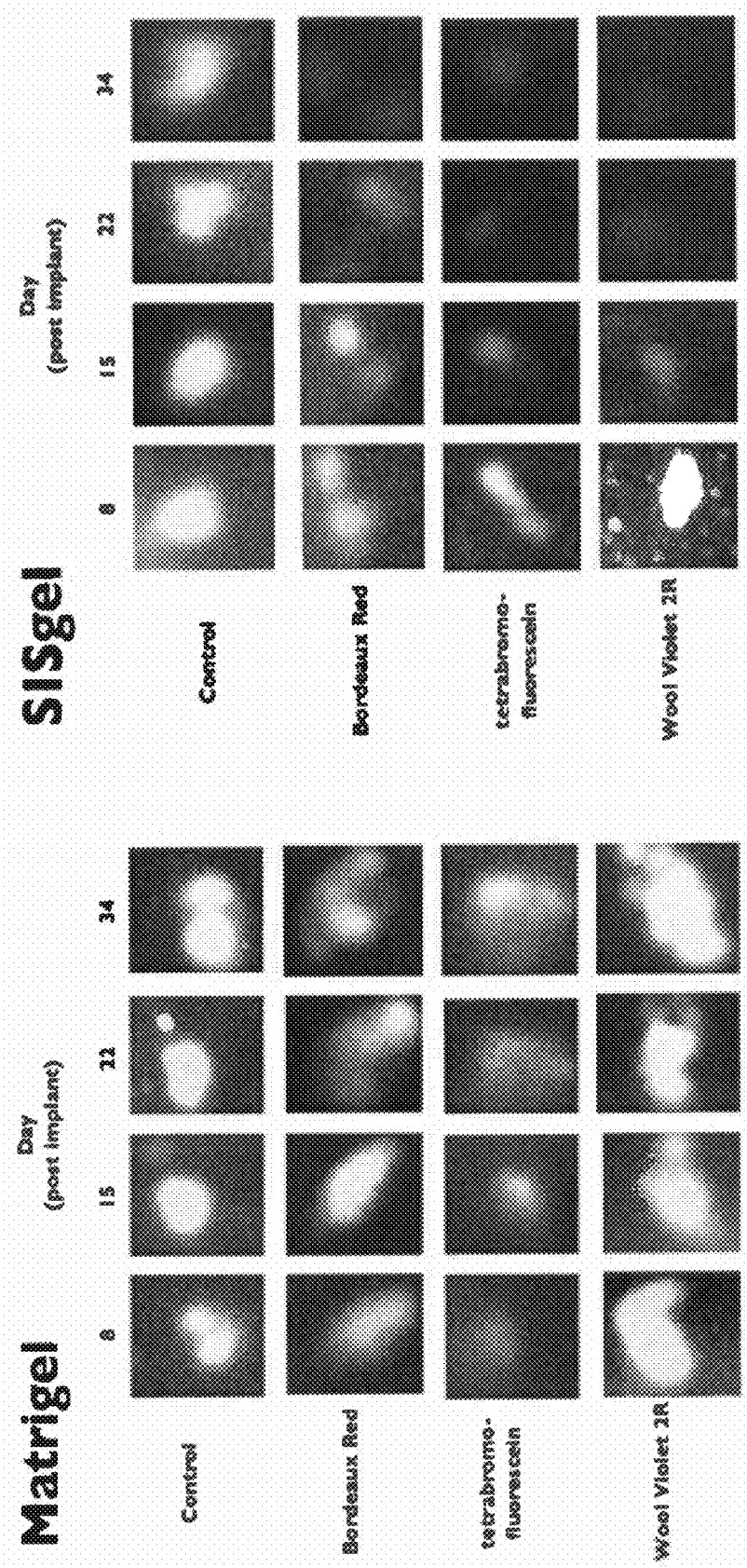
FIG. 10 are photographs showing the effects of three test compounds on cancer cells which have been co-injected with either Matrigel or SISgel under the flank skin of immunogenically-comprised mice in a method of the invention.

An example of an in vivo screening method of the invention is shown in FIG. 10. In this experiment, the activities of three compounds identified by the in vitro screening method were compared against both ECM-suppressed (SISgel, right) and actively growing (Matrigel, left) J82 metastatic bladder cancer cells. J82 metastatic bladder cancer cells were implanted into the flank of mice ((immunogenically compromised (nude) mice purchased from Jackson Labs)) in either a permissive (Matrigel) or suppressive (SISgel) matrix. GFP-tagged cells ($5 \times 10^7$) were injected into the lateral flank of male athymic mice with 4-5 mice per treatment group. When tumors were first visible fluorescently (8 days after implantation), 35 mg/kg Bordeaux Red, tetrabromofluorescein, or Wool Violet 2R were injected Monday, Wednesday and Friday and tumor size was measured using fluorescence microscopy. A representative time course of fluorescence imaging is shown from a single animal for each treatment group. Note that all three compounds caused disappearance of the cells suppressed by the co-injected SISgel whereas none of the three compounds had any activity against the actively growing cells (which were co-injected with Matrigel). The SISgel controls, which were not treated with any anti-cancer test compound, clearly remained alive without actively growing for 34 days, whereas the Matrigel controls continued to grow. One agent, tetrabromofluorescein, showed a weak inhibition of tumor growth in the Matrigel treated animals in that the rate of growth was lower in the animals treated with this compound than in the controls or animals treated with the other compounds.

These data clearly demonstrate the efficacy of the present in vivo screening method as a test for identifying in vivo activity against ECM-suppressed cancer cells and thus against micrometastatic cells in vivo.

Utility

In addition to the in vitro and in vivo screening methods described above, the present invention further contemplates a method for the treatment of a patient afflicted with cancer or who may have suppressed metastatic cancer cells or conditions characterized at least wherein such disease states or conditions may be treated by the administration of a therapeutically effective amount of a compound of the present invention as described hereinabove to a subject in need thereof.

A therapeutically effective amount of a compound of the present invention refers to an amount which is effective in controlling, reducing, or suppressing the growth or expression of a cancer cell, particularly a suppressed metastatic cancer cell. The term "controlling" is intended to refer to all processes wherein there may be a slowing, suppressing, interrupting, arresting, or stopping of the progression of the disease and does not necessarily indicate a total elimination of all disease symptoms.

The term "therapeutically effective amount" is further meant to define an amount resulting in the improvement of any parameters or clinical symptoms characteristic of cancer. The actual dose will be different for the various specific molecules, and will vary with the patient's overall condition, the seriousness of the symptoms, and counter indications.

As used herein, the term "subject" or "patient" refers to a warm blooded animal such as a mammal which is afflicted with a particular cancer. It is understood that guinea pigs, dogs, cats, rats, mice, horses, cattle, sheep, zoo animals, llamas, livestock, and humans are examples of animals within the scope of the meaning of the term.

A therapeutically effective amount of the compound used in the treatment described herein can be readily determined by the attending diagnostician, as one of ordinary skill in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount of a compound of the present invention also refers to an amount of the compound which is effective in controlling, reducing or eliminating cancer or another condition described herein.

A therapeutically effective amount of the compositions of the present invention will generally contain sufficient active ingredient (e.g., NSC 191384, NSC 191384D-1, NSC 191384D-2, NSC 191384D-3, NSC 606532, NSC 697726, and NSC140377 shown in FIGS. 3A and 3B, and Wool Violet 2R, 3,4,5,6-tetrabromofluorescein, and Bordeaux Red shown in FIGS. 6A-6C) (or any salt, ester, or derivative thereof) to deliver from about 0.1 µg/kg to about 100 mg/kg (weight of active ingredient/body weight of patient). Preferably, the composition will deliver at least 0.5 µg/kg to 50 mg/kg, and more preferably at least 1 µg/kg to 10 mg/kg.

Practice of the method of the present invention comprises administering to a subject a therapeutically effective amount of the active ingredient, in any suitable systemic or local formulation, in an amount effective to deliver the dosages listed above. An effective, particularly preferred dosage of a positive compound (for example, NSC 191384, NSC 191384D-1, NSC 191384D-2, NSC 191384D-3, NSC 606532, NSC 697726, NSC140377, Wool Violet 2R, 3,4,5,6-tetrabromofluorescein, and Bordeaux Red) for substantially inhibiting suppressed cancer cells is 1 µg/kg to 1 mg/kg of the active ingredient. The dosage can be administered on a one-time basis, or (for example) from one to five times per day or once or twice per week, or continuously via a venous drip, depending on the desired therapeutic effect.

As noted, preferred amounts and modes of administration are able to be determined by one of ordinary skill in the art. One of ordinary skill in the art of preparing formulations can readily select the proper form and mode of administration depending upon the particular characteristics of the compound selected, the disease state to be treated, the stage of the disease, and other relevant circumstances using formulation technology known in the art, described, for example, in Remington's Pharmaceutical Sciences, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally, intrarectally, or parenterally (i.e., subcutaneously, intravenously, intramuscularly, intraperitoneally, or intratracheally).

For oral and intrarectal administration, the compounds can be formulated into solid or liquid preparations such as capsules, suppositories, pills, tablets, lozenges, melts, liposomes, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety. Topical administration is also intended to refer to intrarectal administration which causes a topical effect on the intraluminal surface.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients will usually be present in the carrier or excipient in a weight ratio of from about 1:1000 to 1:20,000, but are not limited to ratios within this range. Preparation of compositions for local use are detailed in Remington's Pharmaceutical Sciences, latest edition, (Mack Publishing).

Additional pharmaceutical methods may be employed to control the duration of action. Increased half-life and controlled release preparations may be achieved through the use of polymers to conjugate, complex with, or absorb the anticancer compounds described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation in order to control release.

For example, the duration of action of the drugs by use of controlled release preparations may be accomplished by incorporation of the test compound or its functional derivatives into particles of a polymeric material such as polyesters, polyamides, polyamino acids, hydrogels, poly(lactic acid), ethylene vinylacetate copolymers, copolymer micelles of, for example, PEG and poly(1-aspartamide).

It is also possible to entrap the test compounds in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of Remington's Pharmaceutical Sciences.

U.S. Pat. No. 4,789,734 describes methods for encapsulating biochemicals in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", Drug Carriers in Biology and Medicine, pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a test compound composition in accordance with this invention, used not only for therapeutic purposes but also for reagent, screening, or diagnostic purposes as known in the art, or for tissue culture. The pharmaceutical preparation intended for therapeutic use should contain a "pharmaceutically acceptable" or "therapeutically effective amount" of a test compound, i.e., that amount necessary for preventative or curative health measures. If the pharmaceutical preparation is to be employed as a reagent or diagnostic, then it should contain reagent or diagnostic amounts of a test compound.

All of the assay methods listed herein are well within the ability of one of ordinary skill in the art given the teachings provided herein.

The present invention is not to be limited in scope by the specific embodiments described herein, since such embodiments are intended as but single illustrations of one aspect of the invention any functionally equivalent embodiments are within the scope of this invention. Indeed, various modifications of the methods of the invention in addition to those shown and described herein will become apparent to those skilled in the art from the foregoing description.

All references, articles, patents, and pending patent applications cited herein are hereby expressly incorporated herein in their entireties by reference.

What is claimed is:

1. A method of identifying a compound which is able to preferentially target suppressed micrometastatic cancer cells over non-suppressed micrometastatic cancer cells, comprising:
   providing labeled cancer cells comprising a fluorescent label;
   providing a malignant phenotype-suppressing matrix;
   injecting, in a test animal, a first portion of the labeled cancer cells and the malignant phenotype suppressing matrix thereby producing an injected test animal having a suppressed population of malignant phenotype cancer cells;
   injecting, in a control animal, a second portion of the labeled cancer cells without the malignant phenotype suppressing matrix thereby producing an injected control animal having a non-suppressed population of malignant phenotype cancer cells;
   treating the injected test animal and injected control animal with a test compound and incubating said labeled cancer cells within the injected test animal and injected control animal; and
   measuring the injected test animal and injected control animal for fluorescence emitted from the labeled cancer cells therein, and wherein when the fluorescence measured from the injected control animal exceeds the fluorescence measured from the injected test animal, the test compound is shown to preferentially target suppressed micrometastatic cancer cells over non-suppressed micrometastatic cancer cells.

2. The method of claim 1 wherein the malignant phenotype-suppressing matrix produced from a mammalian source comprising an extracellular matrix, including the small intestine, large intestine, stomach, lung, liver, glands, kidney, pancreas, placenta, heart, bladder, and prostate.

3. The method of claim 1 wherein the control animal is co-injected with cancer cells and a malignant phenotype permissive matrix.

4. The method of claim 3 wherein the malignant-phenotype permissive matrix is matrigel.

5. The method of claim 1 wherein the test animal is immunogenically-compromised.

6. The method of claim 1 wherein the cancer cells comprise cells from bladder cancer, liver cancer, breast cancer, lung cancer, prostate cancer, pancreatic cancer, colon cancer, and/or melanoma.

7. The method of claim 1 wherein the cancer cells comprise cells selected from the group consisting of bladder cells, transitional cells, squamous cells, small cell carcinoma cells, medullary cells, cells of adenocarcinomas, and cells of basal cell carcinomas.

8. A method of identifying a compound which is able to preferentially target suppressed micrometastatic cancer cells over non-suppressed micrometastatic cancer cells, comprising:
   providing a test animal comprising labeled cancer cells which have a fluorescent label and wherein the test animal has been injected with a malignant phenotype suppressing matrix causing suppression of the labeled cancer cells thereby producing a suppressed population of malignant phenotype cancer cells in the test animal;
   providing a control animal having a non-suppressed population of malignant phenotype cancer cells comprising the labeled cancer cells;
   treating the test animal and control animal with a test compound and incubating said labeled cancer cells within the test animal and control animal; and
   measuring the test animal and control animal for fluorescence emitted from the labeled cancer cells therein, and wherein when the fluorescence measured from the control animal exceeds the fluorescence measured from the test animal, the test compound is shown to preferentially target suppressed micrometastatic cancer cells over non-suppressed micrometastatic cancer cells.

9. The method of claim 8 wherein the malignant phenotype-suppressing matrix produced from a mammalian source comprising an extracellular matrix, including the small intestine, large intestine, stomach, lung, liver, glands, kidney, pancreas, placenta, heart, bladder, and prostate.

10. The method of claim 8 wherein the control animal has been injected with a malignant phenotype permissive matrix.

11. The method of claim 10 wherein the malignant-phenotype permissive matrix is matrigel.

12. The method of claim 8 wherein the test animal is immunogenically-compromised.

13. The method of claim 8 wherein the labeled cancer cells comprise cells from bladder cancer, liver cancer, breast cancer, lung cancer, prostate cancer, pancreatic cancer, colon cancer, and/or melanoma.

14. The method of claim 8 wherein the labeled cancer cells comprise cells selected from the group consisting of bladder cells, transitional cells, squamous cells, small cell carcinoma cells, medullary cells, cells of adenocarcinomas, and cells of basal cell carcinomas.

15. A method of treating micrometastatic cancer cells in a subject in need of such treatment, comprising:
   providing a composition comprising:
      at least one of Wool Violet 2R, 3,4,5,6-tetrabromofluorescein, and Bordeaux Red; and
      a pharmaceutically acceptable carrier; and
   administering the composition to the subject.

16. The method of claim 15 wherein the micrometastatic cancer cells comprise cells from at least one of bladder cancer, liver cancer, breast cancer, lung cancer, prostate cancer, pancreatic cancer, colon cancer, and melanoma.

17. The method of claim 15 wherein the micrometastatic cancer cells comprise cells selected from the group consisting of bladder cells, transitional cells, squamous cells, small cell carcinoma cells, medullary cells, cells of adenocarcinomas, and cells of basal cell carcinomas.

* * * * *

UNITED STATES PATENT AND TRADEMARK OFFICE
CERTIFICATE OF CORRECTION

PATENT NO.        : 8,101,159 B2  
APPLICATION NO.   : 12/540821  
DATED             : January 24, 2012  
INVENTOR(S)       : Robert E. Hurst and Michael A. Ihnat Page 1 of 1

It is certified that error appears in the above-identified patent and that said Letters Patent is hereby corrected as shown below:

Column 2, line 31: Delete "MDA-breast" and replace with -- MDA-MD-468 breast --

Signed and Sealed this
Eighth Day of May, 2012

David J. Kappos
*Director of the United States Patent and Trademark Office*